(12) United States Patent
Zeng

(10) Patent No.: US 12,419,393 B2
(45) Date of Patent: Sep. 23, 2025

(54) PAINLESS SLOW-EXPANDING PIERCING NEEDLE AND METHOD FOR USING SAME

(71) Applicant: Biao Zeng, Hunan (CN)

(72) Inventor: Biao Zeng, Hunan (CN)

( * ) Notice: Subject to any disclaimer, the term of this patent is extended or adjusted under 35 U.S.C. 154(b) by 147 days.

(21) Appl. No.: 18/281,764

(22) PCT Filed: Sep. 23, 2021

(86) PCT No.: PCT/CN2021/119753
§ 371 (c)(1),
(2) Date: Sep. 12, 2023

(87) PCT Pub. No.: WO2022/217837
PCT Pub. Date: Oct. 20, 2022

(65) Prior Publication Data
US 2024/0148406 A1     May 9, 2024

(30) Foreign Application Priority Data
Apr. 16, 2021   (CN) .......................... 202110409481.1

(51) Int. Cl.
  *A44C 7/00*       (2006.01)
  *A44C 15/00*      (2006.01)
  *A61B 17/34*      (2006.01)
  *A61M 29/00*      (2006.01)

(52) U.S. Cl.
  CPC .......... *A44C 7/001* (2013.01); *A44C 15/0035* (2013.01); *A61B 17/3417* (2013.01); *A61M 29/00* (2013.01); *A61B 2017/3454* (2013.01)

(58) Field of Classification Search
  CPC . A61B 17/3217; A61B 17/34; A61B 17/3417; A61B 2017/3454; A61M 29/00; A44C 15/0035; A44C 7/00; A44C 7/001
  See application file for complete search history.

(56) References Cited

U.S. PATENT DOCUMENTS

| | | | |
|---|---|---|---|
| 2,739,596 A | | 3/1956 | Roberts |
| 3,527,223 A | * | 9/1970 | Melvin .................. A44C 7/001 |
| | | | 606/188 |

(Continued)

FOREIGN PATENT DOCUMENTS

| | | |
|---|---|---|
| CN | 201719367 U | 1/2011 |
| CN | 203563786 U | 4/2014 |

(Continued)

*Primary Examiner* — Sarah A Long

(57) ABSTRACT

A painless slow-expanding piercing needle and a method for using same are disclosed. The painless slow-expanding piercing needle includes: a piercing needle with a diameter not greater than 0.3 mm; and a wire having a first end and a second end. The first end has a greater diameter than second end, the second end is connected to the piercing needle, and the first end is curled into a spiral tube shape. After piercing from one side to form a wound, the piercing needle is separated from second end, and the second end is curled into a spiral tube shape and curled up at the other side of the wound. After the wound heals, uncurling the first end by a length, moving the wire toward the second end to a proper position and curling the first and the second ends tightly are performed for several times until hole expansion is achieved.

8 Claims, 4 Drawing Sheets

(56) References Cited

U.S. PATENT DOCUMENTS

| | | | | |
|---|---|---|---|---|
| 2010/0063532 A1* | 3/2010 | Moore | ............... | A61F 5/56 |
| | | | | 606/199 |
| 2017/0105494 A1* | 4/2017 | Sencer | ............... | A44C 7/00 |
| 2020/0163799 A1* | 5/2020 | Nathan | ............ | A61F 11/00 |

FOREIGN PATENT DOCUMENTS

| CN | 105191341 | A | 12/2015 |
|---|---|---|---|
| CN | 108618285 | A | 10/2018 |
| CN | 208159764 | U | 11/2018 |
| CN | 113081198 | A | 7/2021 |
| GB | 1247653 | A | 9/1971 |
| JP | 2009153786 | A | 7/2009 |

* cited by examiner

PAINLESS SLOW-EXPANDING PIERCING NEEDLE AND METHOD FOR USING SAME

TECHNICAL FIELD

The present disclosure relates to the technical field of body piercing, and in particular to a painless slow-expanding piercing needle and a method for using same.

BACKGROUND

A traditional piercing needle with a thickness of 0.8-4 mm is a single hollow needle body or a trocar with a plastic sleeve. The needle selected for piercing must be slightly thicker than or of the same thickness as a jewelry rod, to facilitate direct introduction of jewelry after piercing. A piercing site may be rich in nerves or blood vessels, resulting in that anesthetic is even required for some piercings due to intolerable pains, and excessive bleeding frequently occurs during some piercings since the wound and the jewelry rod cannot fit closely. The thicker the needle, the easier it is to accidentally injure blood vessels and nerves. The introduction of a jewelry rod into the wound often results in a failed piercing due to misoperations, and the wound after the introduction of jewelry often suffers from severe pain or continuous bleeding due to foreign body irritation.

After a body piercing, epithelial tissue is first formed on an inner wall of a hole to protect the wound, and connective tissue also forms a relatively tough and firm lumen under the epithelial tissue to support the jewelry. The wound may accommodate a foreign body for several months, making the wound care troublesome.

The smaller the hole, the easier it is for the epithelial tissue to heal. When the epithelial tissue has just healed and the connective tissue has not yet formed, the hole is loose and extremely elastic and can be enlarged remarkably. Thus, it is very easy and safe to expand the hole at this stage.

SUMMARY

An object of the present disclosure is to provide a painless slow-expanding piercing needle and a method for using same. By using the painless slow-expanding piercing needle, the problems in the existing technology of strong piercing pain, excessive bleeding, susceptibility to infection, long duration of pain, slow wound recovery, and troublesome long-term care are alleviated.

In order to achieve the above object, the present disclosure provides a technical solution as follows:

a painless slow-expanding piercing needle, including:
a piercing needle with a diameter not greater than 0.3 mm; and
a wire having a first end and a second end, where the first end has a greater diameter than the second end, the second end is connected to the piercing needle, and the first end is curled into a spiral tube shape;
after piercing from one side to form a wound, the piercing needle is separated from the second end, and the second end is curled into a spiral tube shape and curled up at the other side of the wound of a user; and after the user's wound heals, uncurling the first end by a certain length, moving the wire toward the second end to a proper position and curling the first end and the second end tightly are performed for several times until hole expansion is achieved.

Based on above-mentioned technical solutions, the present disclosure can also be improved as follows.

Further, the painless slow-expanding piercing needle further includes a wire curling rod which has a third end and a fourth end, where the third end has a smaller diameter than the fourth end, the wire curling rod is used for curling the first end and the second end of the wire into a spiral tube shape and can assist in introducing a jewelry rod, the first end is curled into a first spiral tube, and the second end is curled into a second spiral tube.

Further, the diameter of the fourth end of the wire curling rod is not less than that of the jewelry rod.

Further, the diameter of the first end of the wire is greater than that of the third end of the wire curling rod and is less than that of the fourth end of the wire curling rod, and after the slow expansion is completed, the wire curling rod is further used for ejecting the wire.

Further, the wire curling rod is made of a hard, non-toxic and non-brittle material.

Further, the diameter of the second end of the wire is not greater than that of the piercing needle.

Further, the diameter of the first end of the wire is greater than that of the piercing needle, to facilitate hole expansion and capillary closure during piercing.

Further, the wire has a length greater than 10 cm.

A method for using a painless slow-expanding piercing needle, including:
S101, curling a first end of a wire into a first spiral tube, and piercing with the piercing needle;
S102, pulling the wire to a proper position, and separating the piercing needle from a second end;
S103, curling the second end of the wire into a second spiral tube, where both ends of the wire are of a spiral tube shape and are curled up on two sides of a wound of a user;
S104, after the wound of the user heals, inserting a wire curling rod into the first spiral tube to uncurl the first spiral tube by a small length, pulling the wire to a proper position, and then tightly curling the second end and the first end; and
S105, repeating the operations in S104 to slowly move the wire in a hole to the first end, so as to achieve painless hole expansion.

Further, the method also includes:
S106, ejecting the wire by means of the wire curling rod, and then ejecting the wire curling rod by means of the jewelry rod.

The present disclosure has the following advantages.

The painless slow-expansion piercing needle in the present disclosure is extremely fine, and can effectively avoid stimulation on pain nerve endings during piercing, so that a person experiencing piercing basically feels no pain or feels slight pain; after the piercing, both ends of the wire are curled into a spiral tube shape until the wound of the user heals; and after the wound heals, the wire is gradually moved to the first end to achieve slow expanding. Therefore, the problems in the existing technology of strong piercing pain, excessive bleeding, susceptibility to infection, long duration of pain, slow wound recovery, and troublesome long-term care are alleviated.

BRIEF DESCRIPTION OF THE DRAWINGS

In order to illustrate the embodiments of the present disclosure or the technical solutions in the existing technology more clearly, the accompanying drawings to be used in the description of the embodiments or existing technology will be briefly described below. Obviously, the accompanying drawings in the following description are some of the embodiments of the present disclosure, and other accompanying drawings may be obtained in accordance with these drawings without creative effort for those of ordinary skill in the art.

Figure 1:
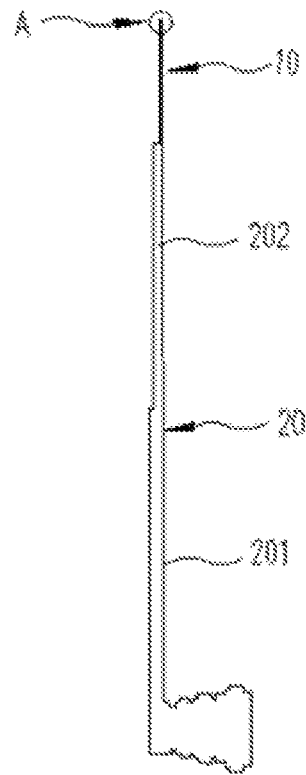
FIG. 1 is a schematic view of an overall structure of a painless slow-expansion piercing needle in an embodiment of the present disclosure.
Figure 2:
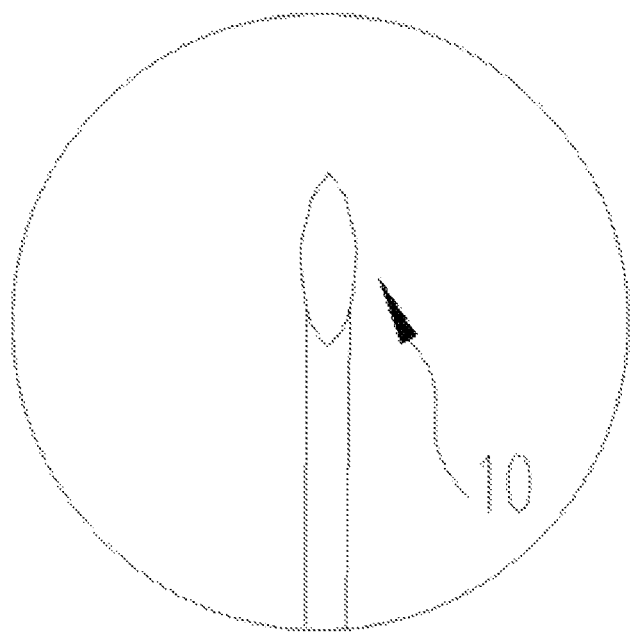
FIG. 2 is an enlarged view of the structure at A.
Figure 3:
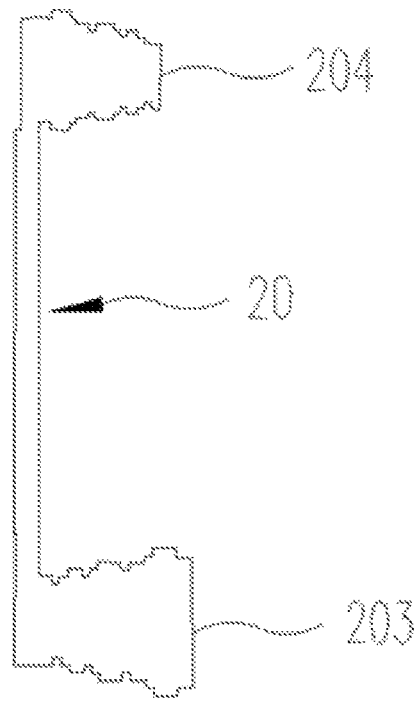
FIG. 3 is a schematic view of a use state of the painless slow-expansion piercing needle in an embodiment of the present disclosure.
Figure 4:
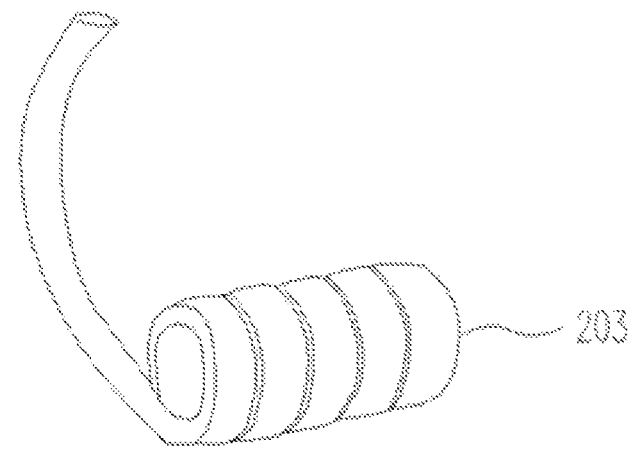
FIG. 4 is a schematic structural view of a hollow spiral tube in an embodiment of the present disclosure.

DESCRIPTION OF REFERENCE NUMERALS piercing needle 10, wire 20, first end 201, second end 202, first spiral tube 203, second spiral tube 204, and wire curling rod 30.

DETAILED DESCRIPTION

The technical solutions of the present disclosure will be clearly and completely described below in conjunction with the embodiments. Obviously, the described embodiments are part of the embodiments of the present disclosure, but not all of them. Based on the embodiments of the present disclosure, all other embodiments obtained by a person of ordinary skill in the art without making creative efforts belong to the scope of protection of the present disclosure.

Embodiment One

As shown in FIGS. 1-5, a painless slow-expansion piercing needle includes a piercing needle 10.

The piercing needle 10 has a diameter not greater than 0.3 mm. When the needle is fine enough to effectively prevent from stimulating pain nerve endings, the human brain basically feels no pain. By means of the piercing needle 10, the problem of intolerable pains when piercing, which even requires anesthetic, can be effectively prevented.

The painless slow-expanding piercing needle is a tool for body piercing. The use of an extremely fine needle for piercing can minimize the injury and pain, reduce operation difficulty, and increase success rate.

The painless slow-expansion piercing needle further includes a wire 20. The wire 20 has a first end 201 and a second end 202. The first end 201 has a greater diameter than the second end 202, the second end 202 is detachably connected to the piercing needle 10, and the first end 201 is curled into a spiral tube shape. After piercing from one side to form a wound, the piercing needle 10 is separated from the second end 202, and the second end 202 is curled into a spiral tube shape and curled up at the other side of the wound of a user. After the wound heals, uncurling the first end 201 by a certain length, moving the wire 20 toward the second end 202 to a proper position and curling the first end 201 and the second end 202 tightly are performed for several times until hole expansion is achieved.

The wire 20 may be made of a variety of soft, flexible, non-toxic and body-resistant materials, and certain special metals such as sterling silver have a sterilizing and disinfecting effect and can better promote wound healing than other materials, making them ideal for use as post-piercing wound healing materials. Preferably, the wire 20 is made of sterling silver.

The painless slow-expansion piercing needle is composed of three parts: a piercing needle 10, a wire 20 and a wire curling rod 30. The piercing needle 10 has a diameter of not greater than 0.3 mm. The wire 20 is a filament with a thick end and a thin end, with the thick end being curled into a spiral tube shape, and the thin end being connected to the piercing needle 10. The wire curling rod 30 is a small stainless-steel rod with one end thick and the other thin.

Anesthetic is not required during piercing with the extremely fine piercing needle 10, and the piercing is almost painless. Low requirements are posed on an operator' piercing skills, and the operator can carry out a slow piercing, and can immediately carry out a piercing again in case of a mistake. After piercing, the wire 20 is pulled to a position with a greater diameter than the needle to close capillaries. Thus, the piercing is almost bloodless, and is not likely to accidentally injure blood vessels and nerves, resulting in a small and tight wound which is less susceptible to infection. It takes at most several weeks for the wound to recover, and the recovery is almost painless. In addition, there is no need to place jewelries directly in the wound. After the wound heals, jewelries can be placed in the hole many times without failure.

Figure 5:
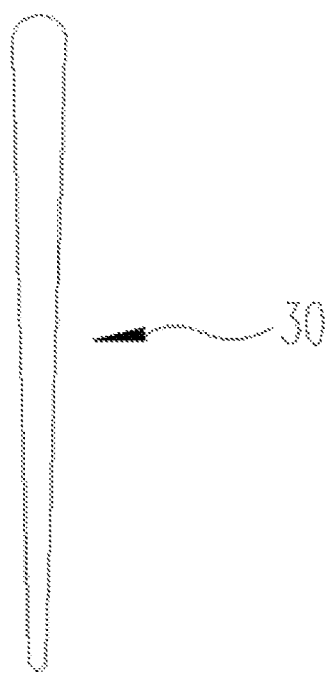
FIG. 5 is a schematic structural view of a wire curling rod in an embodiment of the present disclosure.

Based on above-mentioned technical solutions, the present disclosure can also be improved as follows:

As shown in FIG. 5, the painless slow-expanding piercing needle further includes a wire curling rod 30 which has a third end and a fourth end. The third end has a smaller diameter than the fourth end. The wire curling rod 30 is used for curling the wire 20 into a hollow spiral tube shape and can assist in introducing a jewelry rod. By means of the wire curling rod 30, the first end 201 is curled into a first spiral tube 203, and the second end 202 is curled into a second spiral tube 204.

Further, the diameter of the fourth end of the wire curling rod 30 is not less than that of the jewelry rod.

Further, the diameter of the first end 201 of the wire 20 is greater than that of the third end of the wire curling rod 30 and is less than that of the fourth end of the wire curling rod 30. After the slow expansion is completed, the wire curling rod 30 is further used for ejecting the wire 20.

Further, the wire curling rod 30 is made of a hard, non-toxic and non-brittle material.

Further, the wire 20 is a metallic sterling silver wire.

Further, the piercing needle 10 is a medical hollow piercing needle 10.

Further, the diameter of the second end 201 of the wire 20 is not greater than that of the piercing needle 10.

Further, the diameter of the first end 201 of the wire 20 is greater than that of the piercing needle 10, to facilitate hole expansion and capillary closure during piercing.

Further, the wire 20 has a length greater than 10 cm.

Figure 6:
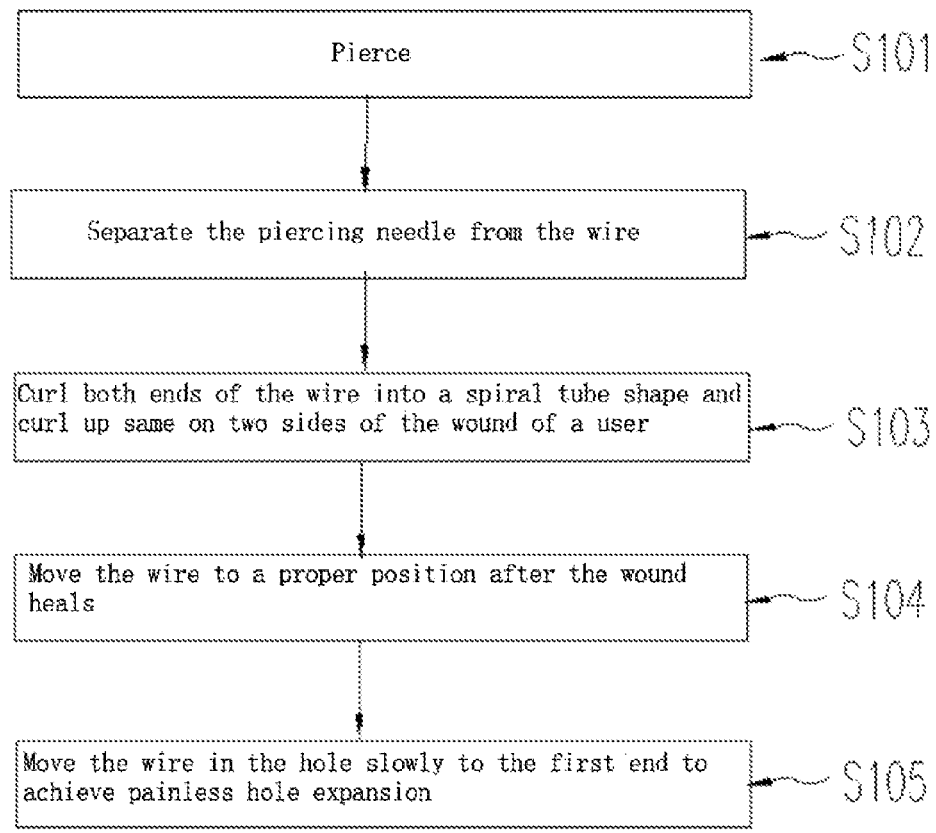
FIG. 6 is a flow chart of a method for using a painless slow-expansion piercing needle in an embodiment of the present disclosure.
Figure 7:
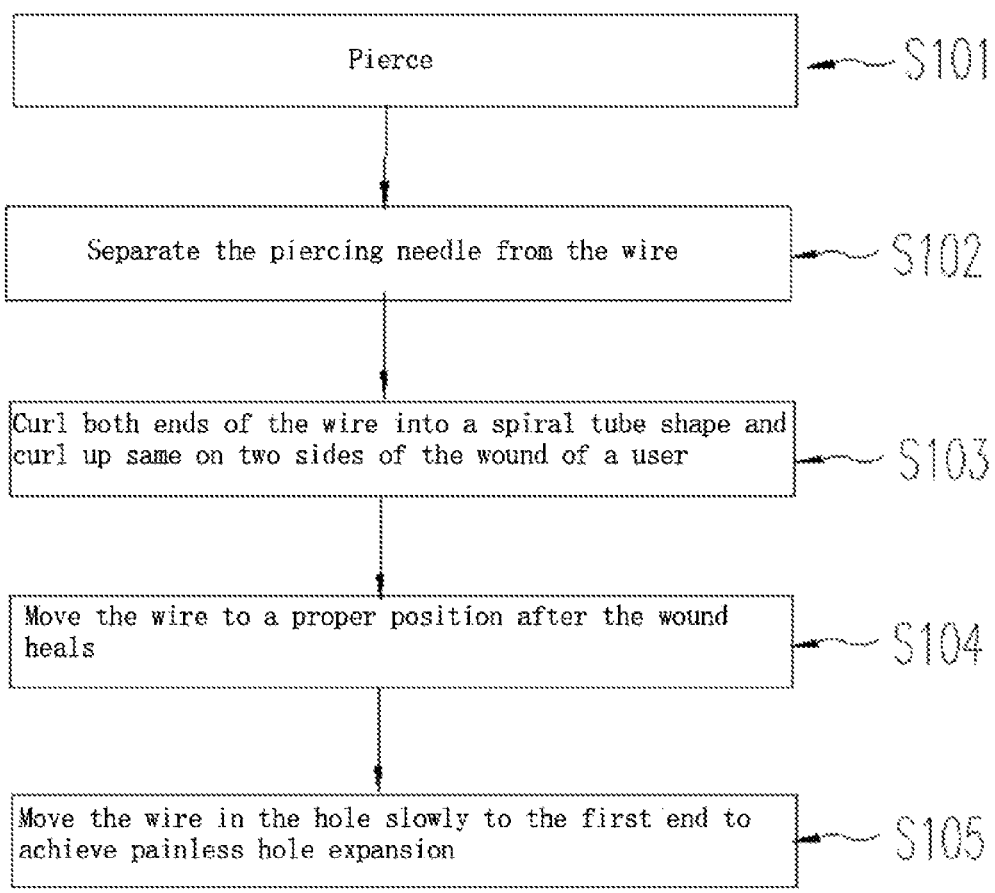
FIG. 7 is a flow chart of a method for using a painless slow-expansion piercing needle in an embodiment of the present disclosure.

As shown in FIGS. 6-7, a method for using a painless slow-expanding piercing needle includes:

S101, piercing;
  in this step, a first end 201 of a wire 20 is curled into a first spiral tube 203, and piercing is carried out with the piercing needle 10;
S102, separating the piercing needle from the wire;

in this step, the wire 20 is pulled to a proper position, and the piercing needle 10 is separated from a second end 202;

S103, curling both ends of the wire into a spiral tube shape and curling up same on two sides of a user's wound;

in this step, the second end 202 of the wire 20 is curled into a second spiral tube 204, where both ends of the wire 20 are of a spiral tube shape and are curled up on two sides of the wound;

S104, after the wound heals, moving the wire to a proper position;

in this step, after the wound heals, a wire curling rod 30 is inserted into the first spiral tube 203 to uncurl the first spiral tube 203 by a small length, the wire 20 is pulled to a proper position, and then the second end 202 and the first end 201 are tightly curled;

S105, slowly moving the wire in a hole to the first end, to achieve painless hole expansion;

in this step, the operations in S104 are repeated to slowly move the wire 20 in the hole to the first end 201, to achieve painless hole expansion; and S106, putting on jewelry;

in this step, the wire 20 is ejected by means of the wire curling rod 30, and then the wire curling rod 30 is ejected by means of a jewelry rod.

In embodiment one, the process of using the painless slow-expansion piercing needle is as follows:

when in use, an operator curls the first end 201 of the wire 20 into the first spiral tube 203, and after piercing using the piercing needle 10, the wire 20 is pulled to a proper position. Then, the piercing needle 10 is separated from the second end 202, the second end 202 is curled into the second spiral tube 204, and both ends of the wire 20 in the spiral tube shape are curled up on two sides of the wound. After the wound heals, the wire curling rod 30 is inserted into the first spiral tube 203 to uncurl the first spiral tube 203 by a small length, the wire 20 is pulled to a proper position, the second end 202 and the first end 201 are then tightly wound, and the above-mentioned operations are repeated multiple times to slowly move the wire 20 in a hole to the thick end, so as to achieve painless hole expansion. Finally, the wire 20 is ejected by means of the wire curling rod 30 (the third end of the wire curling rod 30 is thinner than the second end 201 of the wire 20, and the fourth end of the wire curling rod 30 is thicker than the second end 201 of the wire 20), and then the wire curling rod 30 is ejected by means of the jewelry rod (the jewelry rod is slightly thinner than or has the same thickness as the fourth end of the wire curling rod 30). If the jewelry rod is not thicker than the first end 201 of the wire 20, the wire 20 can be ejected directly with the jewelry rod. If the above-mentioned operations fail, the third end of the wire curling rod 30 can be inserted into the piercing hole for operation again. The use of medical lubricant can make the operations easier and smoother.

Embodiment Two

In this embodiment, the same reference numerals are used to indicate the same structures as in embodiment one and the same description is omitted. Embodiment two has made improvements based on embodiment one in that the piercing needle 10 and the wire 20 can be integrally connected, and the wire 20 is made of human body-resistant soft alloy. A front end of the wire 20 is quenched and hardened and used as the piercing needle 10. When the piercing is completed, the front end is cut off, and the second end 202 of the wire 20 is curled into a spiral tube shape and curled up at the other side of the wound.

In embodiment two, the process of using the painless slow-expansion piercing needle is as follows:

when in use, an operator curls the first end 201 of the wire 20 into a first spiral tube 203, the wire 20 is pulled to a proper position after piercing using the piercing needle 10, the front end of the wire 20 is cut off, and the second end 202 of the wire 20 is curled into a spiral tube shape and curled up at the other side of the wound. The remaining steps are the same as that in embodiment one, and the same description is omitted.

In the description of the present disclosure, it is to be understood that the orientation or positional relationships indicated by terms "center", "longitudinal", "transverse", "length", "width", "thickness", "upper", "lower", "front", "back", "left", "right", "vertical", "horizontal", "top", "bottom", "inner", "outer", "clockwise", "counterclockwise", etc., are based on the orientation or positional relationships shown in the accompanying drawings, which are only intended to facilitate the description of the present disclosure and simplify the description, rather than indicate or imply that the device or element referred to must have a specific orientation and be constructed and operated in a specific orientation, and therefore are not to be construed as limiting the present disclosure.

In addition, the terms "first", "second" and the like are used for descriptive purposes only and are not to be understood as indicating or implying relative importance or implicitly specifying the number of technical features indicated. Thus, a feature defined with "first" and "second" may expressly or implicitly include one or more of the described features. In the description of the present disclosure, "a plurality of" means two or more, unless otherwise expressly and specifically limited. Furthermore, the terms "installation", "connected" and "connection" are to be understood in a broad sense. For example, the connection may be a fixed connection, a detachable connection, or an integral connection; a mechanical connection or an electrical connection; a direct connection, or an indirect connection through an intermediate component; or an internal communication between two components. Those of ordinary skill in the art can understand the specific meanings of the above terms in the present disclosure according to specific situations.

Finally, it should be noted that the above embodiments are only used to illustrate and are not intended to limit the technical solutions of the present disclosure. Although the present disclosure has been described in detail with reference to the foregoing embodiments, those of ordinary skill in the art should understand that modifications may still be made to the technical solutions described in the foregoing embodiments, or equivalent replacements may be made to some or all of the technical features. These modifications or replacements do not make the essence of the corresponding technical solutions depart from the scope of the technical solutions of the various embodiments of the present disclosure.

The invention claimed is:

1. A painless slow-expanding piercing needle, comprising:
a piercing needle with a diameter not greater than 0.3 mm;
a wire having a first end and a second end, wherein the first end has a greater diameter than the second end, the second end is connected to the piercing needle, and the first end is curled into a spiral tube shape;

a wire curling rod which has a third end and a fourth end, wherein the third end has a smaller diameter than the fourth end, the wire curling rod is used for curling the first end and the second end of the wire into the spiral tube shape and can assist in introducing a jewelry rod, wherein the first end is curled into a first spiral tube, and the second end is curled into a second spiral tube; and wherein after piercing from one side to form a wound, the piercing needle is separated from the second end, and the second end is curled into a spiral tube shape and curled up at the other side of the wound of a user; and after the wound is healed, uncurling the first end by a certain length, moving the wire toward the second end to a proper position and curling the first end and the second end tightly are performed for several times until hole expansion is achieved.

2. The painless slow-expanding piercing needle of claim 1, wherein the diameter of the fourth end of the wire curling rod is not less than a diameter of the jewelry rod.

3. The painless slow-expanding piercing needle of claim 2, wherein the diameter of the first end of the wire is greater than the diameter of the third end of the wire curling rod and is less than the diameter of the fourth end of the wire curling rod, and after slow expansion is completed, the wire curling rod is further used for ejecting the wire.

4. The painless slow-expanding piercing needle of claim 1, wherein the wire curling rod is made of a hard, non-toxic and non-brittle material.

5. The painless slow-expanding piercing needle of claim 1, wherein the diameter of the second end of the wire is not greater than the diameter of the piercing needle.

6. The painless slow-expanding piercing needle of claim 1, wherein the diameter of the first end of the wire is greater than the diameter of the piercing needle, to facilitate slow expansion and capillary closure during piercing.

7. The painless slow-expanding piercing needle of claim 1, wherein more than one wire is provided, and an additional individual wire not connected to the piercing needle is thicker and can be used for subsequent larger hole expansion.

8. The painless slow-expanding piercing needle of claim 1, wherein the wire has a length greater than 10 cm.

* * * * *